United States Patent
Hung et al.

(10) Patent No.: US 11,141,428 B2
(45) Date of Patent: Oct. 12, 2021

(54) OCTASACCHARIDES AND USES THEREOF

(71) Applicant: Academia Sinica, Taipei (TW)

(72) Inventors: Shang-Cheng Hung, Taipei (TW);
Kenji Kadomatsu, Nagoya (JP);
Kazuma Sakamoto, Nagoya (JP);
Yen-Chun Ko, Taipei (TW);
Cheng-Fang Tsai, Taipei (TW);
Chiao-Yuan Fan, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 16/771,643

(22) PCT Filed: Dec. 12, 2018

(86) PCT No.: PCT/US2018/065057
§ 371 (c)(1),
(2) Date: Jun. 10, 2020

(87) PCT Pub. No.: WO2019/118525
PCT Pub. Date: Jun. 20, 2019

(65) Prior Publication Data
US 2021/0113608 A1    Apr. 22, 2021

Related U.S. Application Data

(60) Provisional application No. 62/597,474, filed on Dec. 12, 2017.

(51) Int. Cl.
*A61K 31/737* (2006.01)
*A61P 25/00* (2006.01)
*C08B 37/00* (2006.01)

(52) U.S. Cl.
CPC .......... *A61K 31/737* (2013.01); *A61P 25/00* (2018.01); *C08B 37/006* (2013.01)

(58) Field of Classification Search
None
See application file for complete search history.

(56) References Cited

U.S. PATENT DOCUMENTS 9,951,149 B2 * 4/2018 Liu ........................ C08L 5/10

OTHER PUBLICATIONS

Silva, Cancers 2020, 12, 3461. (Year: 2020).*

* cited by examiner

*Primary Examiner* — Layla D Berry
(74) *Attorney, Agent, or Firm* — NZ Carr Law Office PLLC

(57) ABSTRACT

Disclosed herein is a sulfated octasacchande of formula (I), a pharmaceutically acceptable salt, solvate or ester thereof: wherein $R^1$ is —NHAc or —NHSO$_3$H; and $R^2$ and $R^3$ are independently H, or —SO$_3$H. Also encompasses herein is a method of treating neuron injury and/or diseases associated with a disrupted autophagy flux. The method includes administering an effective amount of the sulfated octasaccharide of formula (I) to a subject in need of such treatment.

11 Claims, 1 Drawing Sheet

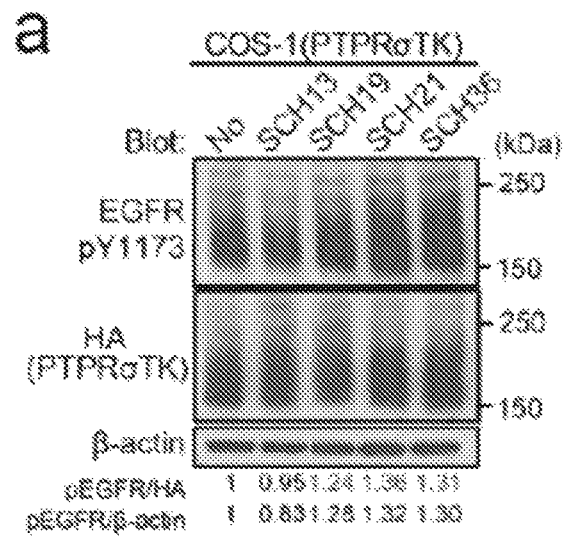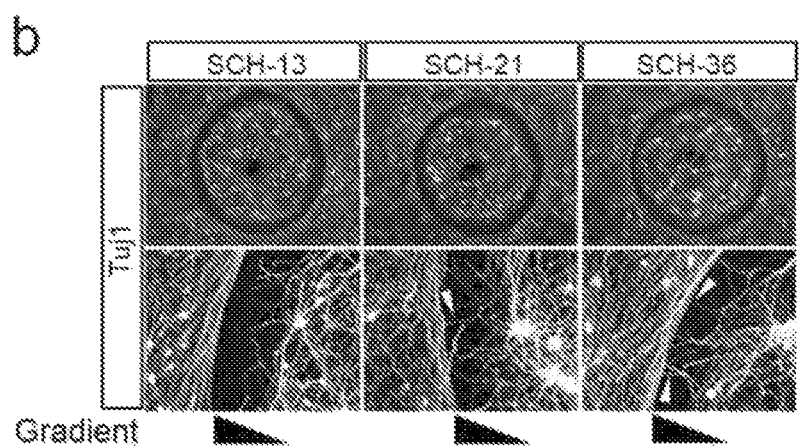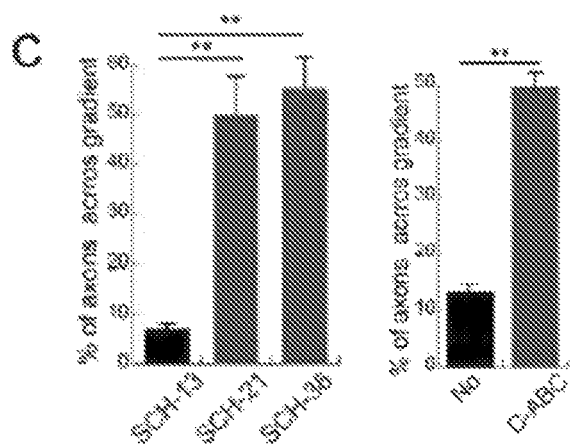

OCTASACCHARIDES AND USES THEREOF

CROSS-REFERENCE TO RELATED APPLICATIONS

This application is a national stage filing under 35 U.S.C. 371 of International Application PCT/US2018/065057, filed Dec. 12, 2018, which claims priority to U.S. Provisional Application No. 62/597,474, filed on Dec. 12, 2017, the content of which is hereby incorporated by reference herein.

BACKGROUND OF THE INVENTION

1. Field of the Invention

The present disclosure in general relates to novel sulfated octasaccharides and uses thereof.

2. Description of Related Art

Inventors of the present invention unexpectedly identify some novel sulfated octasaccharides may bind to receptor-type protein tyrosin phosphatase (RPTP), which regulates neuronal outgrowth and guidance and participating in excitatory synapse formation and maintenance. Accordingly, these novel sulfated octasaccharides are useful for the development of medicaments for the treatment of neuronal injuries and/or diseases associated with a disrupted autophagy flux.

In addition, these novel sulfated octasaccharides may also bind to the surface of cholangio-cancerous cells, thus they are also useful for making prognosis on whether a subject is at risk of developing cholangiocarcinoma.

SUMMARY OF THE INVENTION

In view of above, the present disclosure provides novel sulfated octasaccharides and treatments of neuron injury and/or diseases associated with a disrupted autophagy flux, as well as methods for making prognosis on whether a subject has or is at risk of having a cholangiocarcinoma.

Accordingly, the first aspect of the present disclosure is directed to a sulfated octasaccharide of formula (I), a pharmaceutically acceptable salt, solvate or ester thereof:

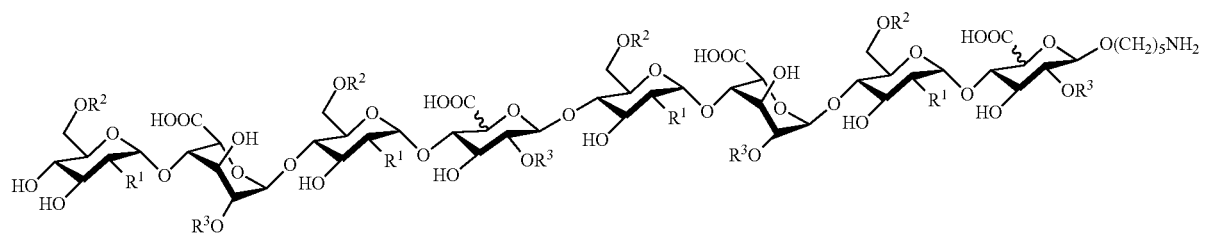

(I)

wherein R is —NHAc or —NHSO$_3$H; and R$^2$ and R$^3$ are independently H, or —SO$_3$H.

According to some embodiments of the present disclosure, in the formula (I), R$^1$ is —NHAc; and R$^2$ and R$^3$ are independently —SO$_3$H.

According to other embodiments of the present disclosure, in the formula (I), R$^1$ is —NHSO$_3$H, R$^2$ is H, and R$^3$ is —SO$_3$H.

According to further embodiments of the present disclosure, in the formula (I), R$^1$ is —NHSO$_3$H; and R$^2$ and R$^3$ are independently —SO$_3$H.

According to further embodiments of the present disclosure, in the formula (I), R$^1$ is —NHSO$_3$H, R$^2$ and R$^3$ are independently H.

The second aspect of the present disclosure is directed to a method of inducing the outgrowth of a neuron. The method includes the step of, contacting the neuron with an effective amount of the sulfated octasaccharide of formula (I), wherein, the sulfated octasaccharide binds to receptor-type protein tyrosine phosphatase σ (RPTPσ).

According to some embodiments of the present disclosure, in the formula (I), R$^1$ is —NHAc; and R$^2$ and R$^3$ are independently —SO$_3$H.

According to other embodiments of the present disclosure, in the formula (I), R$^1$ is —NHSO$_3$H, R$^2$ is H, and R$^3$ is —SO$_3$H.

The third aspect of the present disclosure is directed to a method of treating a neuronal injury. The method includes the step of administering to a subject in need of such treatment an effective amount of the sulfated octasaccharide of formula (I) to induce the outgrowth of an injured neuron.

According to some embodiments of the present disclosure, in the formula (I), R$^1$ is —NHAc; and R$^2$ and R$^3$ are independently —SO$_3$H.

According to other embodiments of the present disclosure, in the formula (I), R$^1$ is —NHSO$_3$H, R$^2$ is H, and R$^3$ is —SO$_3$H.

The fourth aspect of the present disclosure is directed to a method of treating a disease associated with a disrupted autophagy flux. The method includes administering to a subject in need of such treatment an effective amount of the sulfated octasaccharide of formula (I) to restore the disrupted autophagy flux in the subject.

According to some embodiments of the present disclosure, in the formula (I), R$^1$ is —NHAc; and R$^2$ and R$^3$ are independently —SO$_3$H.

According to other embodiments of the present disclosure, in the formula (I), R$^1$ is —NHSO$_3$H, R$^2$ is H, and R$^3$ is —SO$_3$H.

According to embodiments of the present disclosure, the disease associated with a disrupted autophagy flux may be a cancer or a neurodegenerative disease.

Examples of the neurodegenerative disease treatable by the present method include, but are not limited to, Amyotrophic lateral sclerosis (ALS), Alzheimer disease (AD), bovine spongiform encephalopathy, Creutzfeldt-Jakob disease (CJD), frontotemporal lobar degeneration, Huntington disease, Lewy body dementia, multiple sclerosis, Parkinson disease (PD), and Pick's disease.

Examples of the cancer treatable by the present method include, but are not limited to, bladder cancer, bone cancer, bone marrow cancer, brain cancer, breast cancer, cholangiocarcinoma, colon cancer, esophagus cancer, gastrointestine cancer, gum cancer, head cancer, kidney cancer, liver cancer, lung cancer, nasopharynx carcinoma, leukemia, neck cancer, ovary cancer, prostate cancer, skin cancer, stomach cancer, testis cancer, tongue cancer, and uterus cancer.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where, FIG. 1: Rescue of dystrophic endballs by sulfated octasaccharides. (a) HS14 and HS6 (10 μg/mL, 15 min) activated RPTPσ. The results of the densitometric analysis are noted at the bottom. (b) HS14 and HS6 (20 μg/mL) rescued dystrophic endball formation and promoted axonal growth (white arrowheads) across an aggrecan gradient (black triangle). (c) Quantification of (b) ($p<0.01$, One-way ANOVA post hoc Duncan's test, for the left graph, $p<0.01$, by Student's t-test for the right graph). Data shown were means+s.e.m. Three mice were used in each treatment group. C-ABC, chondroitinase ABC.

DETAILED DESCRIPTION OF THE PREFERRED EMBODIMENTS

The detailed description provided below in connection with the appended drawings is intended as a description of the present disclosure and is not intended to represent the only forms in which the present disclosure may be constructed or utilized.

1. Definitions

Unless otherwise indicated, the term "patient" or "subject" may be used interchangeably in the present disclosure, and refers to any animal. The animal can be a human subject, or a non-human subject. The subject may be a human, but can also be a mammal in need of veterinary treatment, e.g., domestic animals or game animals, farm animals, and laboratory animals (e.g., rats, mice, guinea pigs, primates, and the like). Usually the animal is a non-human mammal, such as a non-human primate. Non-human primates include chimpanzees, cynomologous monkeys, spider monkeys, and macaques, e.g., Rhesus or Pan. Domestic animals and game animals include cows, horses, pigs, sheep, deer, bison, buffalo, mink, felines (e.g., domestic cats, canines (e.g., dogs)), wolf and fox, avian species (e.g., chicken, turkey, and ostrich), and fish (e.g., trout, catfish, and salmon).

A subject can be one who has been diagnosed with or identified as suffering from neuronal injury or having a disorder associated with a disrupted autophagy flux. A subject can be one that is not currently being treated with an agent described herein (e.g., a sulfated octasaccharide of the present disclosure). A subject can be one who has been previously diagnosed with a disease that is being treated with a therapeutic regimen comprising a sulfated octasaccharide of the present disclosure, wherein the disease is not a disease characterized by neuronal injury or associated with a disrupted autophagy flux.

The term "contacting" is used herein with respect to a cell (e.g., a neuron) and refers to any mode of delivery or "administration" of an agent either to cells or to whole organisms, in which the agent (e.g., a sulfated octasaccharide of the present disclosure) is brought into contact with one or more cells in sufficient amount to exhibit its effects on the cells.

Unless otherwise indicated, the terms "treat," "treating" and "treatment" contemplate an action that occurs while a patient is suffering from the specified disease or disorder, which reduces the severity of the disease or disorder, or one or more of its symptoms, or retards or slows the progression of the disease or disorder.

The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

Exemplary acid addition salts include acetates (such as those formed with acetic acid or tribaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Solvates of the compounds of the present invention are also contemplated herein. The term "solvate" must be understood to mean a complex of variable stoichiometry formed by a solute (e.g., the octasaacharides of formula (I), or a salt thereof) and a solvent. Examples of suitable solvent include, but are not limited to, water, acetone, methanol, ethanol, and acetic acid. Preferably, the solvent used is a pharmaceutically acceptable solvent. Examples of suitable pharmaceutically acceptable solvents include water, ethanol and acetic acid. Most preferably, the solvent is water. The preparation of salts or solvates can be carried out by means of methods known in the art. It must be noted that non-pharmaceutically acceptable salts or solvates are also within the scope of the invention since they can be useful in the preparation of pharmaceutically acceptable salts, solvates or prodrugs.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. The Sulfated Octassacharides of the Present Invention

Aspects of the present disclosure relate to the findings that certain sulfated octasaccharides can induce neuronal outgrowth of a neuron, restore disrupted autophagy flux, and binding to the surfaces of cancerous cells, thus these sulfated octasaccharides are potential candidates for developing medicaments for treating neuron injury or diseases associated with disrupted autophagy flux. Examples of the sulfated octasaccharides are described herein.

In one aspect, the present invention relates to a sulfated octasaccharide of formula (I), a pharmaceutically acceptable salt, solvate or ester thereof:

the working examples. All stereoisomers of the present compounds, such as those which may exist due to asymmetric carbons on the R substituents of the compound of formula (I) including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

3. Method of Use

Some sulfated octasaccharides of the present invention may bind to receptor-type protein tyrosine phosphatase σ (RPTPσ) and induce neuronal outgrowth, thus these sulfated octasaccharides of the present invention are useful as candidates for developing medicaments for treating neuron injury and/or diseases associated with disrupted autophagy flux.

The present invention thus encompasses a method of inducing the outgrowth of a neuron. The method includes, contacting the neuron with an effective amount of the sulfated octasaccharide of formula (I).

The present disclosure also encompasses a method of treating a neuronal injury. The method includes administering to a subject in need of such treatment an effective amount of the sulfated octasaccharide of formula (I) to induce the outgrowth of an injured neuron.

Also encompasses in the present disclosure is a method of treating a disease associated with a disrupted autophagy flux. The method includes administering to a subject in need of such treatment an effective amount of the sulfated octasaccharide of formula (I) to restore the disrupted autophagy flux in the subject.

According to some embodiments of the present disclosure, in any of the methods described above, in the sulfated octasaccharide of formula (I), $R^1$ is —NHAc; and $R^2$ and $R^3$ are independently —SO$_3$H.

According to other embodiments of the present disclosure, in any of the methods described above, in the sulfated octasaccharide of formula (I), $R^1$ is —NHSO$_3$H, R2 is H, and $R^3$ is —SO$_3$H.

(I)

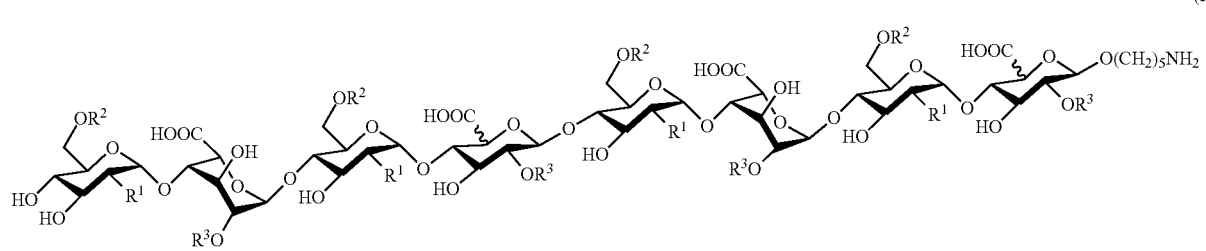

wherein $R^1$ is —NHAc or —NHSO$_3$H; and $R^2$ and $R^3$ are independently H, or —SO$_3$H.

In some embodiments of the present disclosure, $R^1$ is —NHAc; and $R^2$ and $R^3$ are independently —SO$_3$H.

In other embodiments of the present disclosure, $R^1$ is —NHSO$_3$H, $R^2$ is H, and $R^3$ is —SO$_3$H.

In further embodiments of the present disclosure, $R^1$ is —NHSO$_3$H; and $R^2$ and $R^3$ are independently —SO$_3$H.

In still further embodiments of the present disclosure, $R^1$ is —NHSO$_3$H, $R^2$ and $R^3$ are independently H.

The sulfated octasaccharides of the present disclosure may be prepared in accordance with procedures described in According to embodiments of the present disclosure, diseases associated with disrupted autophagy flux may be cancers or neurodegenerative diseases. Examples of the neurodegenerative disease treatable by the present method include, but are not limited to, Amyotrophic lateral sclerosis, Alzheimer disease, bovine spongiform encephalopathy, Creutzfeldt-Jakob disease, frontotemporal lobar degeneration, Huntington disease, Lewy body dementia, multiple sclerosis, Parkinson disease, and Pick's disease.

Examples of the cancer treatable by the present method include, but are not limited to, bladder cancer, bone cancer, bone marrow cancer, brain cancer, breast cancer, cholangiocarcinoma, colon cancer, esophagus cancer, gastrointestine cancer, gum cancer, head cancer, kidney cancer, liver cancer, lung cancer, nasopharynx carcinoma, leukemia, neck cancer, ovary cancer, prostate cancer, skin cancer, stomach cancer, testis cancer, tongue cancer, and uterus cancer.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods

Cell culture. HEK293T (from human embryonic kidney) and COS-1 (from monkey kidney) cells were cultured in Dulbecco's modified eagle's medium (DMEM) supplemented with heat-inactivated 10% fetal calf serum (FCS). Neuro2a cells (established from mouse neuroblastoma) were cultured in RPMI-1640 supplemented with 10% FCS.

SNU478, HuCCT1, Huh28, BxPC3, and HCT8 were respectively cultured in RPMI 1640 (Gibco®, Invitrogen Co., USA) containing 100 U/mL penicillin and 100 g/mL streptomycin (Pen Strep, Gibco®, Invitrogen Co., USA), 10% fetal bovine serum (FBS, Gibco®, Invitrogen Co., USA). KKU100, MMNK1, and HepG2 were espectively cultured in DMEM complemented with 100 U/mL penicillin, 100 g/mL streptomycin and 10% fetal bovine serum. All cells were cultured at 37° C. under an atmosphere containing 5% $CO_2$.

Preparation of an aggrecan gradient spot on coverslip. Glass coverslips were coated with 100 μg/mL PLL overnight at room temperature, rinsed with sterile water and dried completely. Onto the coverslip, 2 μL of an aggrecan (0.4 mg/mL) and laminin (10 μg/mL) mixture in $Ca^{2+}$- and $Mg^{2+}$-free Hank's balanced salt solution (HBSS) (Invitrogen) was spotted and dried. Then, the coverslip was bathed in laminin (10 g/mL) solution in HBSS until just before (i.e., at least 3 h before) cell plating at 37° C. The laminin solution was subsequently removed, and the cells were plated without allowing the surface of the coverslip to dry.

DRG neuron primary culture. DRGs were dissected out of C57BL/6J (SLC) adult (12-16 weeks) female mice. The roots of isolated DRGs were trimmed in cold HBSS, collected in a centrifuge tube and spun down for 1 min at low speed (500 rpm). Then, the HBSS was removed. The tissues were incubated in collagenase-II (4 mg/mL)/dispase-II (4.67 mg/mL) in HBSS for 15 min at 37° C. After spinning down at low speed, the tissues were rinsed once with pre-warmed culture media consisting of Neurobasal-A (Gibco) with Gluta-MAX (Gibco), Anti-Anti (Gibco) and B-27 (Invitrogen), then spun down and triturated in fresh media. To refine neurons, the cell suspension was carefully overlaid onto 15% bovine serum albumin (BSA) in HBSS and spun down for 5 min at high speed (1000 rpm), and the supernatant was gently removed. The DRG cells were rinsed once and suspended in the media. The DRG cells were plated onto coverslips in the media.

For embryonic DRG culture, DRG tissues were isolated from embryonic day 15 (E15) mice in cold HBSS, trimmed in pre-warmed Neurobasal medium (Gibco) and explanted onto laminin coated- or aggrecan/laminin spotted-glass. DRGs were cultured in Neurobasal medium with Gluta-MAX, Anti-Anti, 50 ng/mL Nerve Growth Factor 2.5S (NGF 2.5S, Invitrogen) and 2% B-27 supplement.

Immunostaining. DRG neurons were fixed in ice-cold methanol for 15 min at −30° C. The fixed samples were then rinsed three times with phosphate buffered saline (PBS) and incubated in a blocking solution containing 5% (v/v) goat serum (Vector) and 0.2% (v/v) Triton-X 100 (Sigma) for 90 min at room temperature. For neuron-specific class III β-tubulin (Tuj1) staining, samples were bathed in 1:1000 mouse monoclonal Tuj1 (Covance, 801201) diluted in PBS containing 2.5% (v/v) normal goat serum overnight at 4° C. After three washes with PBS, neurons were incubated with 1:250 Alexa488-conjugated goat anti-mouse IgG (Molecular Probes, A11001) dissolved in PBS containing 2.5% (v/v) goat serum for 2 h at room temperature.

For double labeling of Tuj1 and microtubule-associated protein 1 light chain 3 (LC3), samples were incubated with 1:1000 mouse monoclonal Tuj1 and 1:500 rabbit monoclonal anti-LC3B (Cell Signaling Technology, 3868) dissolved in PBS containing 2.5% (v/v) goat serum overnight at 4° C. After washing, these samples underwent secondary staining procedures with 1:250 Alexa488-conjugated goat anti-mouse IgG and 1:250 Alexa594-conjugated goat anti-rabbit IgG (Molecular Probes, A11012) diluted in PBS containing 2.5% (v/v) goat serum for 2 h at room temperature. The samples were then thoroughly washed with PBS and embedded with FluorSave (Millipore). Fluorescent images were obtained using a BZ-9000 inverted fluorescent microscope (Keyence) equipped with a cooled CCD camera, mercury lamp and proper filter sets. Digital images were processed using PhotoShop CC software (Adobe).

SDS-PAGE and Western blotting. Cells were lysed with Tris-buffered saline (TBS), 1% Triton-X, Complete Mini Protease Inhibitor Cocktail (Roche) and Phostop Phosphatase Inhibitor Cocktail (Roche). Lysates were incubated on ice for 10 min and centrifuged at 20000 g for 10 min at 4° C. Supernatants were mixed with 4×SDS sample buffer and boiled for 5 min.

All samples were run on 5-20% gradient gel (Wako) and transferred to nitrocellulose membranes (GE Healthcare). After blocking with 5% non-fat dry milk or BSA, the membranes were blotted with primary antibodies. Primary antibodies used in this work included anti-EGFR pY1174 (Invitrogen, 44794G), anti-HA (Roche, clone 3F10), 4G10 Platinum (Millipore, 05-1050) and anti-β-actin (Sigma Aldrich, clone AC-15). All primary antibodies were used at 1:1000 dilution. All secondary antibodies conjugated with horseradish peroxidase were from Jackson ImmunoResearch and used at 1:3000 dilution. Membranes were developed with Novex ECL (Invitrogen) or ECL Plus Substrate (Pierce).

Statistical Analysis

No statistical method was used to predetermine sample size of experiments. Data were analyzed and are presented as mean with s.e.m. or s.d. (indicated in each FIGURE legends). Data sets were analyzed using the Student's t-test to compare two populations. In the case of more than two groups, the One-way ANOVA combined with post hoc Duncan's or Tukey test to correct for multiple comparisons was applied. All tests were performed as two-sided. Results with a P-value of 0.05 or less were considered significant. Mean values, s.d., s.e.m. and statistics were calculated with Excel 2013 (Microsoft software). No criteria of inclusion or exclusion of data were used in this study. All samples or animals were included in the analysis. Experiments were carried out without prior randomization of the animals and without blinding. The assumption of normal distribution was not tested. The variance was not compared between groups. No statistical method was used to predetermine sample size of mouse experiments. Data shown are representative of one to four independent experiments as specified in the FIGURE legends.

Example 1 Chemical Synthesis of the Present Sulfated Octasaccharides

The present octasaccharides HS1-HS8 and HS9-HS16 were respectively synthesized in accordance with steps as described in schemes I and II. In general, the sugar backbones were assembled in a convergent manner using disaccharide and tetrasaccharide building blocks with thiotolyl functionality acting as leaving group. The protecting groups employed are according to the pattern used recently for heparin and heparosan synthesis (Hu et al., 2011 Nat. Chem. 3, 557-563; Zulueta et al., 2012 J. Am. Chem. Soc. 134, 8988-8995). With fully protected skeletons, functional group transformations were carried out in a divergent manner (Hu et al., 2012 J. Am. Che. Soc. 134, 20722-20727) to afford differentially sulfonated final products with an aminopentyl aglycon moiety.

Scheme I
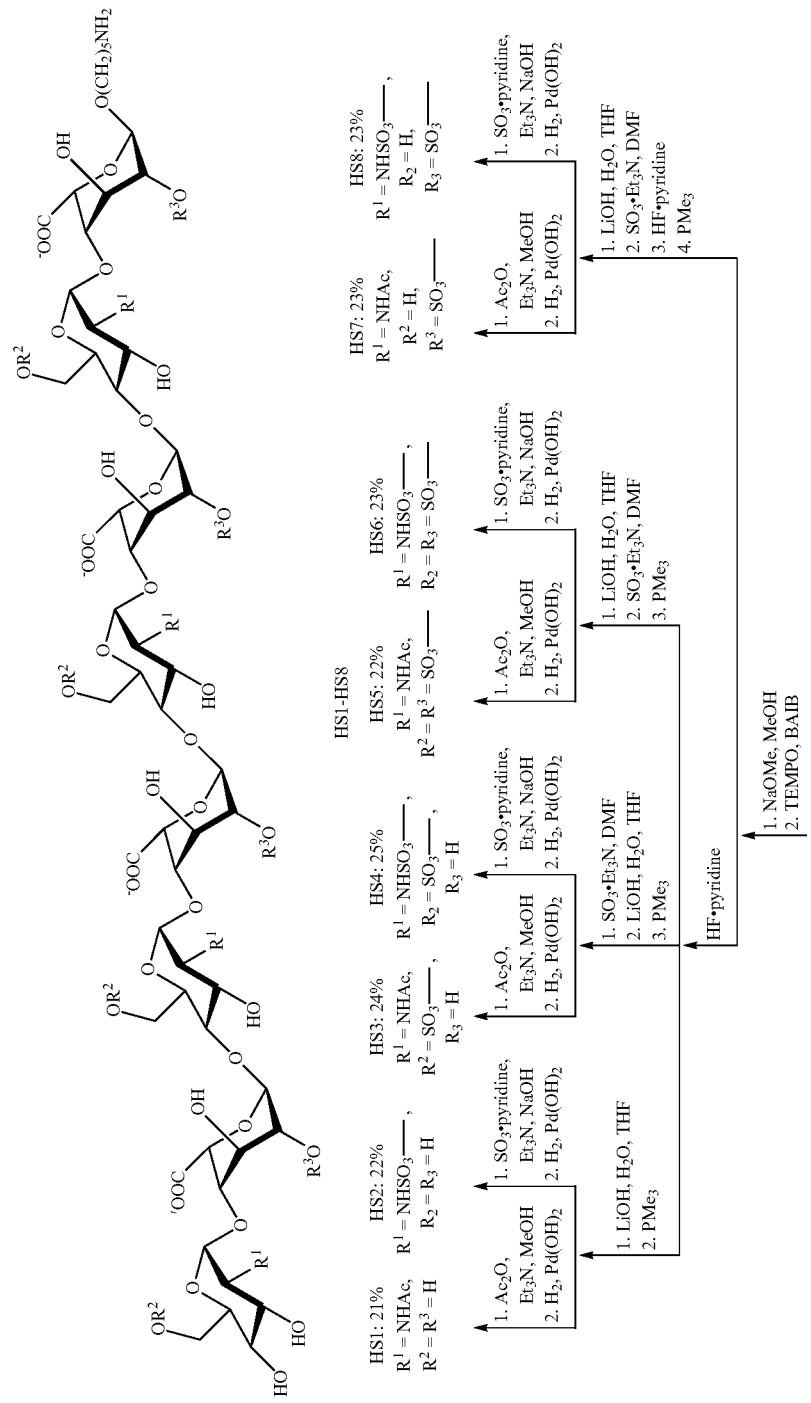

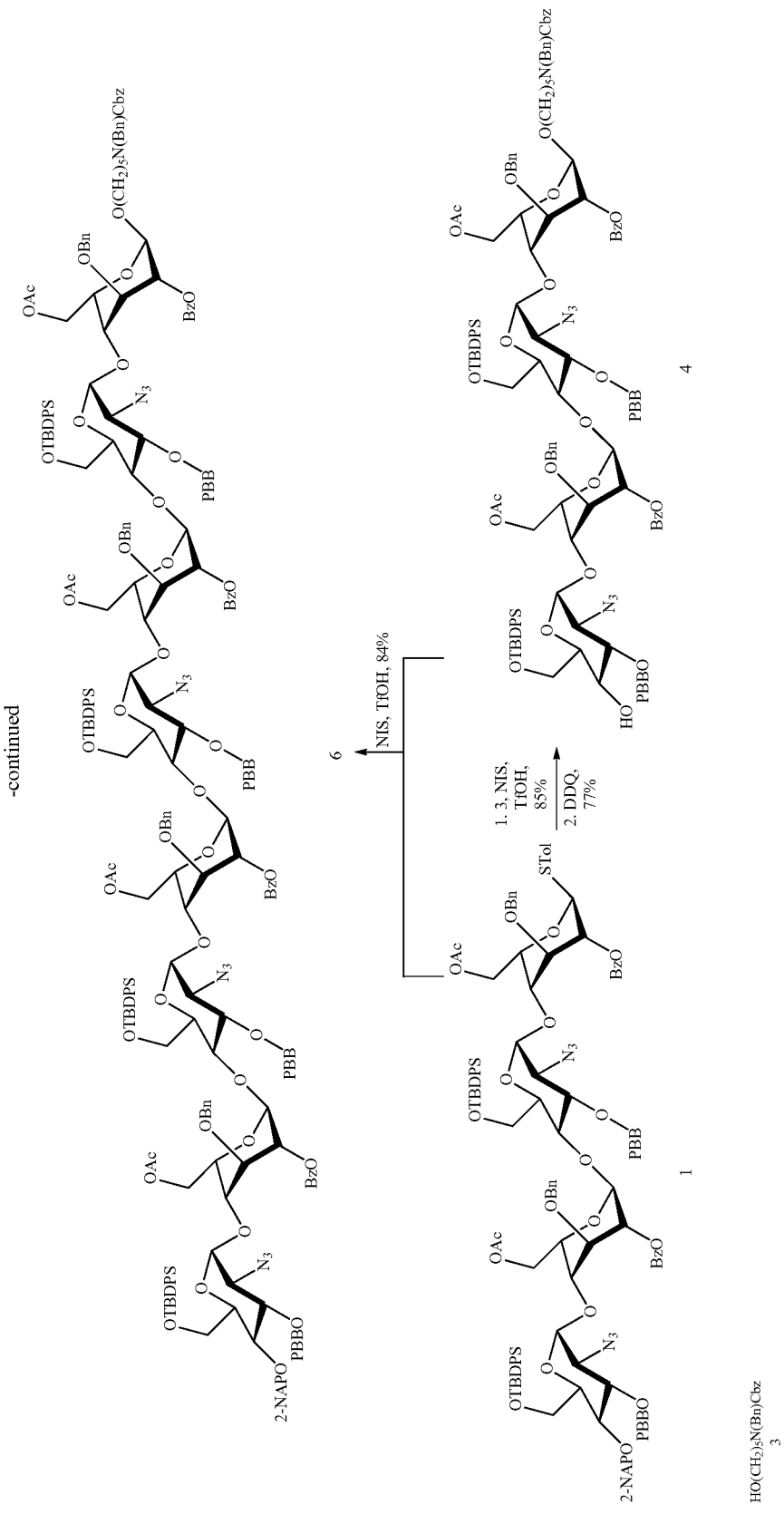

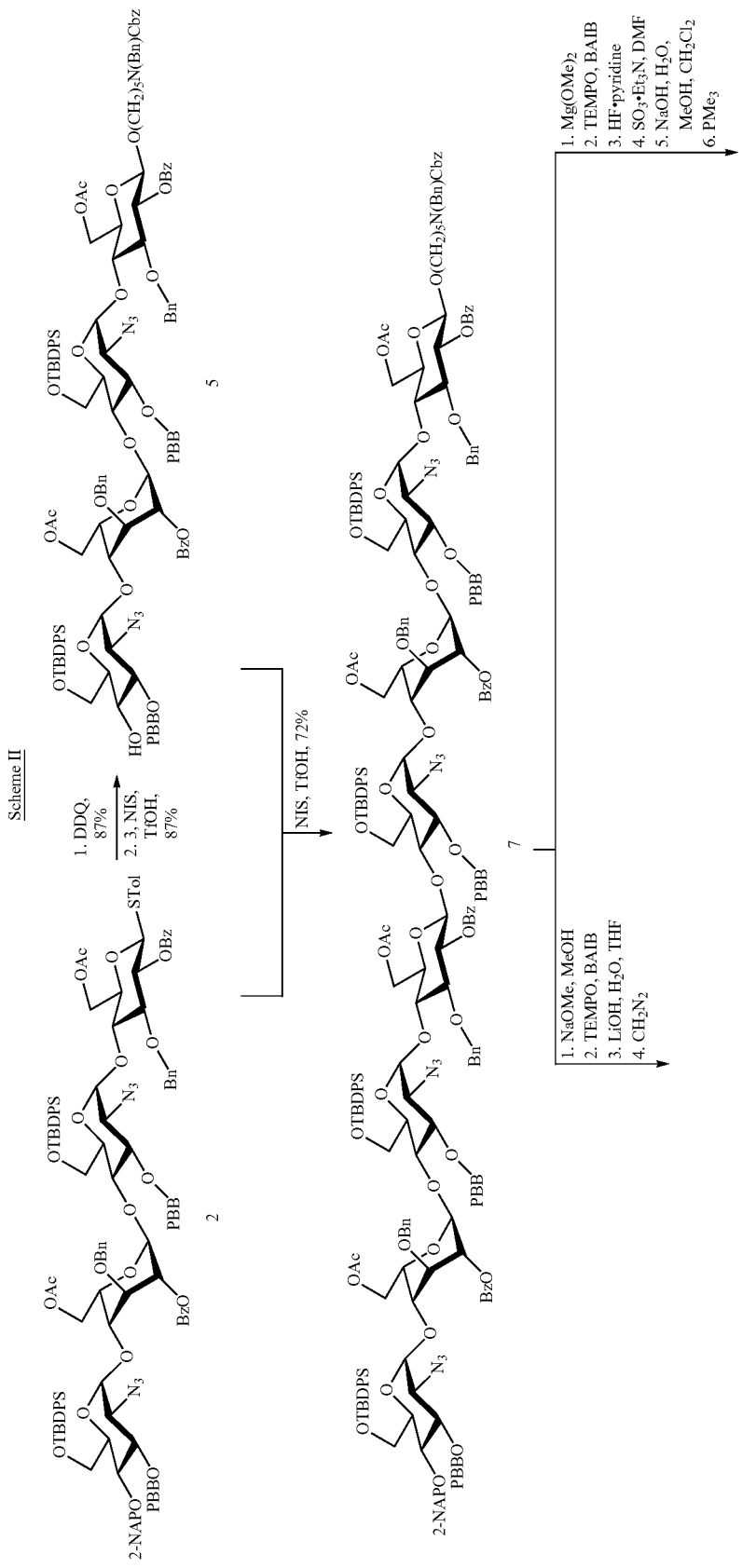

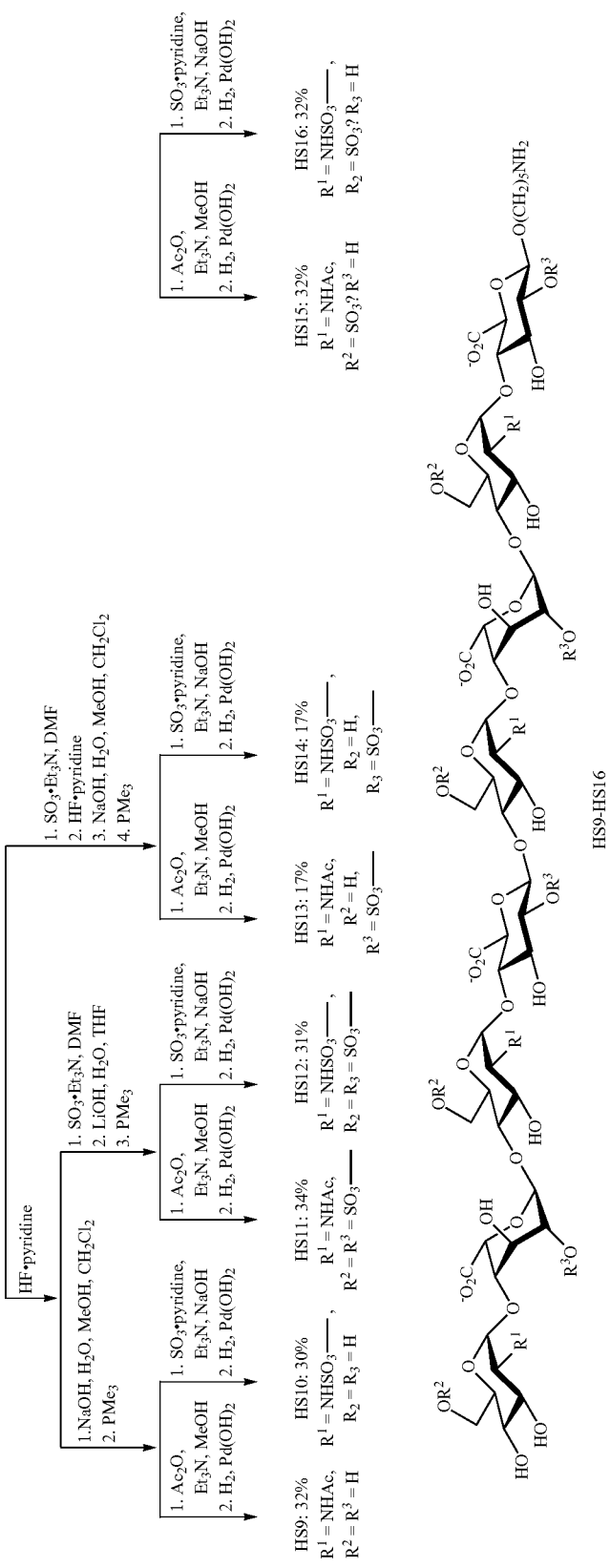

The chemical data of HS1 to HS 16 are provided bellowed.

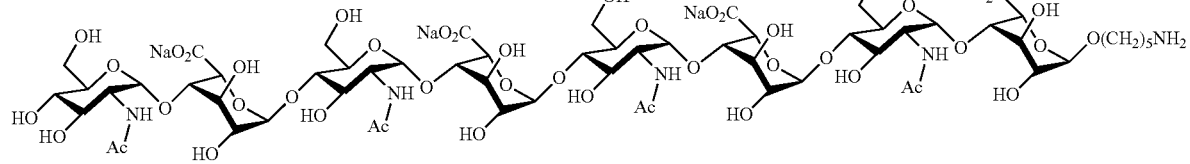

HS1

5-Aminopentyl (2-acetamido-2-deoxy-α-D-glucopyranosyl)-(1→4)-α-L-idopyranosiduronyl-(1→4)-(2-acetamido-2-deoxy-α-D-glucopyranosyl)-(1→4)-α-L-idopyranosiduronyl-(1→4)-(2-acetamido-2-deoxy-α-D-glucopyranosyl)-(1→4)-α-L-idopyranosiduronyl-(1→4)-(2-acetamido-2-deoxy-α-D-glucopyranosyl)-(1→4)-α-L-idopyranosiduronate (HS1). $^1$H NMR (600 MHz, D$_2$O): δ 5.12-5.06 (m, 4H), 4.84-4.82 (m, H), 4.79-4.76 (m, 2H), 4.67-4.63 (m, 3H), 4.42 (d, J=2.8 Hz, 1H), 4.02-3.93 (m, 4H), 3.90-3.83 (m, 5H), 3.83-3.71 (m, 15H), 3.71-3.62 (m, 8H), 3.62-3.53 (m, 4H), 3.53-3.49 (m, 1H), 3.38 (t, J=9.5 Hz, 1H), 2.90 (t, J=7.6 Hz, 2H), 1.94 (s, 3H, Ac), 1.93 (s, Ac×2), 1.92 (s, 3H, Ac), 1.63-1.54 (m, 4H, CH$_2$ linker), 1.40-1.32 (m, 2H, CH$_2$ linker); $^{13}$C NMR (150 MHz, D$_2$O): δ 175.0 (C), 174.9 (C), 174.8 (C), 174.3 (C), 174.28 (C), 174.2 (C), 101.6 (CH), 100.7 (CH), 94.4 (CH), 94.3 (CH), 76.6 (CH), 76.5 (CH), 76.4 (CH), 74.5 (CH), 74.4 (CH), 74.3 (CH), 73.9 (CH), 71.9 (CH), 71.1 (CH), 71.05 (CH), 71.0 (CH), 69.9 (CH), 69.8 (CH), 69.7 (CH), 69.6 (CH), 69.4 (CH), 69.3 (CH), 68.8 (CH), 68.6 (CH), 68.0 (CH$_2$), 60.1 (CH$_2$), 60.0 (CH$_2$), 53.6 (CH), 53.5 (CH), 39.3 (CH$_2$), 28.0 (CH$_2$), 26.2 (CH$_2$), 22.2 (CH$_2$), 21.8 (CH$_3$); HRMS (ESI): m/z calcd for C$_{61}$H$_{95}$N$_5$O$_{45}$ ([M-2H]$^{2-}$) 808.7650, found: 808.7641.

5-Aminopentyl (2-acetamido-2-deoxy-α-D-glucopyranosyl)-(1→4)-α-L-idopyranosiduronyl-(1→4)-(2-acetamido-2-deoxy-α-D-glucopyranosyl)-(1→4)-β-D-glucopyranosiduronyl-(1→4)-(2-acetamido-2-deoxy-α-D-glucopyranosyl)-(1→4)-α-L-idopyranosiduronyl-(1→4)-(2-acetamido-2-deoxy-α-D-glucopyranosyl)-(1→4)-β-D-glucopyranosiduronate (HS9). $^1$H NMR (600 MHz, D$_2$O): δ 5.40 (d, J=3.8 Hz, 1H), 5.38 (d, J=3.8 Hz, 1H), 5.20 (d, J=3.7 Hz, 1H), 5.19 (d, J=3.7 Hz, 1H), 4.94 (d, J=3.7 Hz, 1H), 4.93 (d, J=3.9 Hz, 1H), 4.75 (d, J=3.1 Hz, 1H), 4.74 (d, J=2.9 Hz, 1H), 4.51 (d, J=7.9 Hz, 1H), 4.46 (d, J=8.0 Hz, 1H), 4.10 (t, J=6.8 Hz, 1H), 4.08 (t, J=6.6 Hz, 1H), 3.97-3.95 (m, 1H), 3.95-3.91 (m, 5H), 3.90-3.87 (m, 5H), 3.86-3.83 (m, 7H), 3.83-3.79 (m, 4H), 3.79-3.77 (m, 2H), 3.77-3.76 (m, 2H), 3.76-3.74 (m, 2H), 3.74-3.71 (m, 3H), 3.71-3.69 (m, 4H), 3.69-3.66 (m, 1H), 3.49 (t, J=9.4 Hz, 1H), 3.38 (t, J=8.6 Hz, 1H), 3.31 (t, J=8.6 Hz, 1H), 3.01 (t, J=7.5 Hz, 1H), 2.06 (s, 6H, Ac×2), 2.04 (s, 3H, Ac), 2.03 (s, 3H, Ac), 1.73-1.65 (m, 4H), 1.52-1.43 (m, 2H); $^{13}$C NMR (150 MHz, D$_2$O): δ 176.0 (C), 175.9 (C), 175.82 (C), 175.77 (C), 175.3 (C), 175.24 (C), 175.20 (C), 103.3 (CH), 103.2 (CH), 102.8 (C), 102.7 (CH), 97.95 (CH), 95.4 (CH), 95.3 (CH), 79.1 (CH), 78.1 (CH), 77.91 (CH), 77.87 (CH), 77.7 (CH), 77.5 (CH), 77.3 (CH), 77.19 (CH), 77.17 (CH), 75.6 (CH), 75.3 (CH), 74.5 (CH), 74.4 (CH), 72.9 (CH), 72.1 (CH), 71.7 (CH), 71.03 (CH$_2$), 71.00 (CH), 70.95 (CH), 70.9 (CH), 70.8 (CH), 70.7 (CH), 70.6 (CH), 70.5 (CH), 70.4 (CH), 61.2 (CH$_2$), 60.7 (CH$_2$), 60.6 (CH$_2$), 60.4 (CH$_2$), 54.8 (CH), 54.5 (CH), 54.1 (CH), 40.4 (CH$_2$), 29.1 (CH$_2$), 27.3 (CH$_2$), 22.9 (CH$_2$), 22.9 (CH$_3$); HRMS (ESI): m/z calcd for C$_{61}$H$_{94}$N$_5$Na$_5$O$_{45}$ ([M+5Na-3H]$^{2+}$): 865.7355, found: 865.7357.

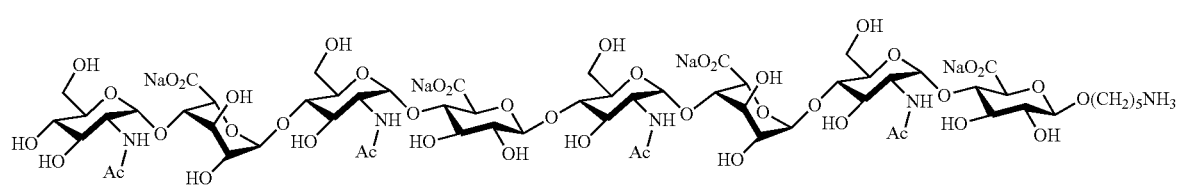

HS9

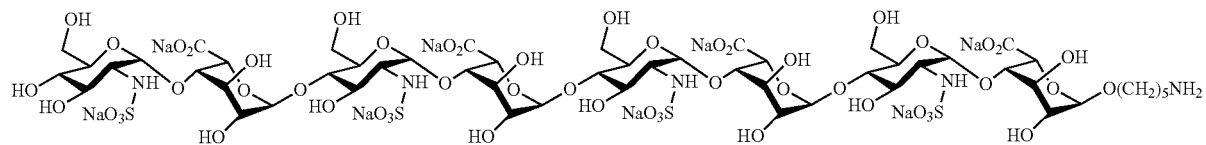

HS2

5-Aminopentyl (2-deoxy-2-sulfamido-α-D-glucopyranosyl)-(1→4)-α-L-idopyranosiduronyl-(1→4)-(2-deoxy-2-sulfamido-α-D-glucopyranosyl)-(1→4)-α-L-idopyranosiduronyl-(1→4)-(2-deoxy-2-sulfamido-α-D-glucopyranosyl)-(1→4)-α-L-idopyranosiduronyl-(1→4)-(2-deoxy-2-sulfamido-α-D-glucopyranosyl)-(1→4)-α-L-idopyranosiduronate (HS2). $^1$H NMR (600 MHz, D$_2$O): δ 5.41-5.35 (m, 4H), 4.98-4.94 (m, 2H), 4.92-4.89 (m, 2H), 4.51 (d, J=1.9 Hz, 1H), 4.16-4.02 (m, 8H), 3.92-3.59 (m, 27H), 3.47 (t, J=9.4 Hz, 1H), 3.28-3.19 (m, 4H), 3.00 (t, J=7.4 Hz, 2H), 1.72-1.63 (m, 2H), 1.48-1.43 (m, 2H); $^{13}$C NMR (150 MHz, D$_2$O): δ 175.2 (C), 101.6 (CH), 100.7 (CH), 95.64 (CH), 95.6 (CH), 95.5 (CH), 95.4 (CH), 77.1 (CH), 77.0 (CH), 76.9 (CH), 74.9 (CH), 74.8 (CH), 74.7 (CH), 71.7 (CH), 71.3 (CH), 71.0 (CH), 70.9 (CH), 69.8 (CH), 69.73 (CH), 69.7 (CH), 69.3 (CH), 69.1 (CH), 69.0 (CH), 68.8 (CH), 68.5 (CH), 68.4 (CH), 68.2 (CH), 68.1 (CH$_2$), 60.2 (CH$_2$), 59.7 (CH$_2$), 58.0 (CH), 57.8 (CH), 39.4 (CH$_2$), 28.0 (CH$_2$), 26.2 (CH$_2$), 22.2 (CH$_2$); HRMS (ESI): m/z calcd for C$_{53}$H$_{86}$N$_5$O$_{53}$S$_4$Na$_3$ ([M+3Na-6H]3-) 611.4177, found: 611.4167.

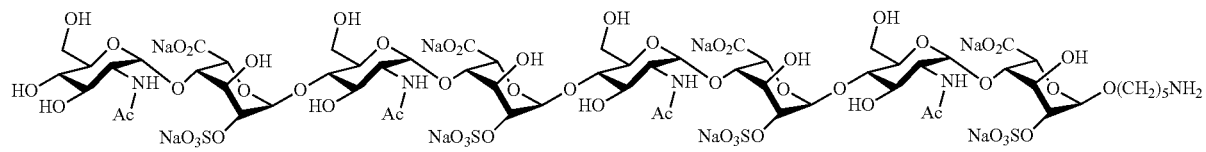

HS7

5-Aminopentyl (2-acetamido-2-deoxy-α-D-glucopyranosyl)-(1→4)-(2-O-sulfonato-α-L-idopyranosiduronyl)-(1→4)-(2-acetamido-2-deoxy-α-D-glucopyranosyl)-(1→4)-(2-O-sulfonato-α-L-idopyranosiduronyl)-(1→4)-(2-acetamido-2-deoxy-α-D-glucopyranosyl)-(1→4)-(2-O-sulfonato-α-L-idopyranosiduronyl)-(1→4)-(2-acetamido-2-deoxy-α-D-glucopyranosyl)-(1→4)-2-O-sulfonato-α-L-idopyranosiduronate (HS7). H NMR (600 MHz, D$_2$O): δ 5.17 (bs, 4H), 5.11-5.08 (m, 4H), 4.90 (d, J=10.1 Hz, 2H), 4.54 (d, J=1.9 Hz, 1H), 4.32 (bs, 3H), 4.30-4.25 (m, 4H), 4.21 (bs, 1H), 4.03-3.96 (m, 9H), 3.90-3.83 (m, 9H), 3.82-3.76 (m, 4H), 3.75-3.67 (m, 8H), 3.45 (t, J=9.3 Hz, 1H), 2.99 (t, J=7.5 Hz, 2H), 2.05 (s, 6H, Ac×2), 2.04 (s, 6H, Ac×2), 1.70-1.61 (m, 4H, CH$_2$ linker), 1.50-1.40 (m, 2H, CH$_2$ linker); $^{13}$C NMR (150 MHz, D$_2$O): δ 175.8 (C), 175.2 (C), 174.8 (C), 174.7 (C), 99.3 (CH), 99.2 (CH), 98.6 (CH), 93.5 (CH), 93.4 (CH), 93.3 (CH), 77.2 (CH), 74.1 (CH), 73.3 (CH), 73.2 (CH), 73.1 (CH), 71.9 (CH), 71.3 (CH), 71.2 (CH), 70.7 (CH), 70.4 (CH), 70.2 (CH), 69.9 (CH), 69.8 (CH), 69.7 (CH), 68.1 (CH$_2$), 67.4 (CH), 67.3 (CH), 67.2 (CH), 64.0 (CH), 63.4 (CH), 63.3 (CH), 63.1 (CH), 60.2 (CH$_2$), 59.7 (CH$_2$), 39.4 (CH$_2$), 27.8 (CH$_2$), 26.2 (CH$_2$), 22.24 (CH$_3$), 22.2 (CH$_3$), 22.1 (CH$_3$); HRMS (ESI): m/z calcd for C$_{61}$H$_{94}$N$_5$O$_{57}$S$_4$ ([M-3H]$^{3-}$) 645.4498, found 645.4489.

HS10

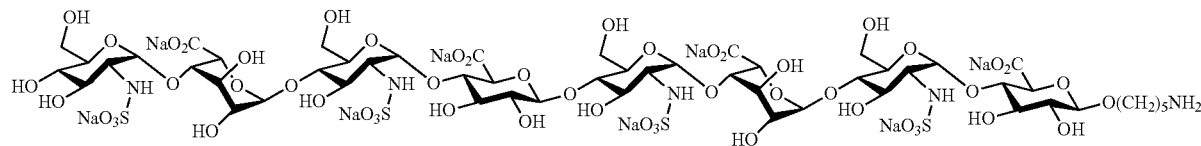

5-Aminopentyl (2-deoxy-2-sulfamido-α-D-glucopyranosyl)-(1→4)-α-L-idopyranosiduronyl-(1→4)-(2-deoxy-2-sulfamido-α-D-glucopyranosyl)-(1→4)-β-D-glucopyranosiduronyl-(1→4)-(2-deoxy-2-sulfamido-α-D-glucopyranosyl)-(1→4)-α-L-idopyranosiduronyl-(1→4)-(2-de oxy-2-sulfamido-α-D-glucopyranosyl)-(1→4)-β-D-glucopyranosiduronate (HS10). $^1$H NMR (600 MHz, D$_2$O): δ 5.62 (d, J=3.7 Hz, 1H), 5.61 (d, J=3.6 Hz, 1H), 5.41 (d, J=3.4 Hz, 1H), 5.39 (d, J=3.4 Hz, 1H), 4.98 (bs, 1H), 4.96 (d, J=2.8 Hz, 1H), 4.55 (d, J=7.9 Hz, 1H), 4.50 (d, J=8.0 Hz, 1H), 4.14-4.07 (m, 4H), 3.94-3.88 (m, 4H), 3.88-3.84 (m, 6H), 3.84-3.81 (m, 7H), 3.81-3.78 (m, 4H), 3.76-3.74 (m, 3H), 3.74-3.70 (m, 4H), 3.68-3.63 (m, 3H), 3.48 (t, J=9.5 Hz, 1H), 3.43 (t, J=8.6 Hz, 1H), 3.36 (t, J=8.6 Hz, 1H), 3.31-3.25 (m, 3H), 3.23 (dd, J=10.3, 3.6 Hz, 1H), 3.02 (t, J=7.5 Hz, 2H), 1.75-1.65 (m, 4H), 1.53-1.43 (m, 2H); $^{13}$C NMR (150 MHz, D$_2$O): δ 176.3 (C), 176.1 (C), 176.0 (C), 103.3 (CH), 103.2 (CH), 102.8 (CH), 102.7 (CH), 98.5 (CH), 98.4 (CH), 96.5 (CH), 96.4 (CH), 78.9 (CH), 78.3 (CH), 78.11 (CH), 78.06 (CH), 77.94 (CH), 77.89 (CH), 77.6 (CH), 77.5 (CH), 76.0 (CH), 75.9 (CH), 73.81 (CH), 73.76 (CH), 72.7 (CH), 72.4 (CH), 71.94 (CH), 71.91 (C), 71.6 (CH), 71.1 (CH$_2$), 70.9 (CH), 70.84 (CH), 70.80 (CH), 70.5 (CH), 70.33 (CH), 70.28 (CH), 70.0 (CH), 69.6 (CH), 61.4 (CH$_2$), 60.81 (CH$_2$), 60.79 (CH$_2$), 60.5 (CH$_2$), 59.3 (CH), 59.0 (CH), 58.6 (CH), 40.5 (CH$_2$), 29.2 (CH$_2$), 27.3 (CH$_2$), 23.0 (CH$_2$); HRMS (ESI): m/z calcd for C$_{53}$H$_{81}$N$_5$Na$_8$O$_{53}$S$_4$ ([M+3Na-6H]$^{3-}$): 611.4177, found: 611.4176; calcd for C$_{53}$H$_{81}$N$_5$Na$_8$O$_{53}$S$_4$ ([M+4Na-7H]$^{3-}$): 618.7449, found: 618.7449.

3.84-3.80 (m, 6H), 3.78-3.66 (m, 6H), 3.48 (t, J=9.3 Hz, 1H), 3.03 (t, J=7.4 Hz, 2H), 2.09 (bs, 3H, Ac), 2.08 (bs, 3H, Ac), 2.07 (bs, 3H, Ac), 2.06 (bs, 3H, Ac), 1.74-1.65 (m, 4H, CH$_2$ linker), 1.56-1.48 (m, 2H, CH$_2$ linker); $^{13}$C NMR (150 MHz, D$_2$O): δ 176.8 (C), 176.4 (C), 175.9 (C), 175.8 (C), 175.7 (C), 175.6 (C), 175.4 (C), 175.3 (C), 101.7 (CH), 101.6 (CH), 100.4 (CH), 100.3 (CH), 98.3 (CH), 98.2 (CH), 94.70 (CH), 94.65 (CH), 81.6 (CH), 81.3 (CH), 80.7 (CH), 78.4 (CH), 77.7 (CH), 77.6 (CH), 77.4 (CH), 77.2 (CH), 76.6 (CH), 76.4 (CH), 74.8 (CH), 74.4 (CH), 73.0 (CH), 72.4 (CH), 72.34 (CH), 72.30 (CH), 71.8 (CH), 71.5 (CH), 71.1 (CH$_2$), 70.9 (CH), 70.6 (CH), 70.5 (CH), 68.6 (CH), 68.5 (CH), 65.1 (CH), 64.4 (CH), 61.4 (CH$_2$), 60.7 (CH$_2$), 60.5 (CH$_2$), 55.1 (CH), 54.5 (CH), 54.1 (CH), 40.5 (CH$_2$), 29.0 (CH$_2$), 27.3 (CH$_2$), 23.3 (CH$_3$), 23.0 (CH$_2$), 22.9 (CH$_3$); HRMS (ESI): m/z calcd for C$_{61}$H$_{91}$N$_5$O$_{57}$S$_4$Na$_8$ ([M+8Na-6H]$^{2+}$): 1058.6221, found: 1058.6226.

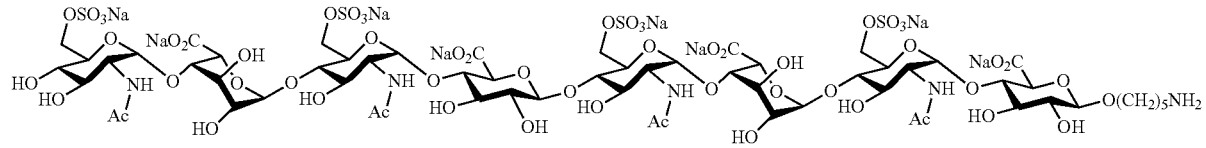

HS15

5-Aminopentyl (2-acetamido-2-deoxy-6-O-sulfonato-α-D-glucopyranosyl)-(1→4)-α-L-idopyranosiduronyl-(1→4)-(2-acetamido-2-deoxy-6-O-sulfonato-α-D-glucopyranosyl)-(1→4)-β-D-glucopyranosiduronyl-(1→4)-(2-acetamido-2-deoxy-6-O-sulfonato-α-D-glucopyranosyl)-(1→4)-α-L-idopyranosiduronyl-(1→4)-(2-acetamido-2-deoxy-6-O-sulfonato-α-D-glucopyranosyl)-(1→4)-β-D-glucopyranosiduronate (HS15). $^1$H NMR (600 MHz, D$_2$O): δ 5.43-5.38 (m, 2H), 5.21-5.18 (m, 2H), 5.01-4.99 (m, 2H), 4.62-4.58 (m, 2H), 4.49-4.46 (m, 2H), 4.39-4.36 (m, 4H), 4.25-4.22 (m, 3H), 4.12-4.10 (m, 3H), 4.02-3.98 (m, 5H), 3.99-3.96 (m, 2H), 3.93-3.91 (m, 2H), 3.85-3.82 (m, 3H), 3.80-3.73 (m, 14H), 3.61-3.57 (m, 2H), 3.39-3.36 (m, 2H), 3.35-3.31 (m, 1H), 3.04-3.00 (m, 2H), 2.07 (bs, 3H, Ac),

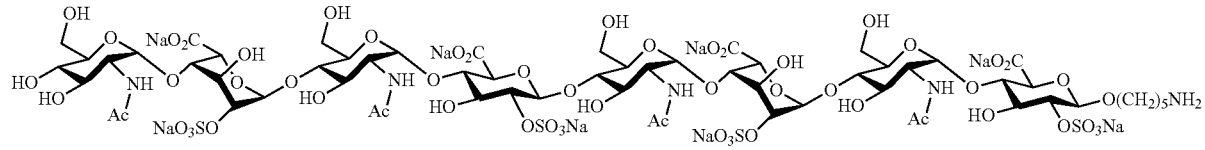

HS13

5-Aminopentyl (2-acetamido-2-deoxy-α-D-glucopyranosyl)-(1→4)-(2-O-sulfonato-α-L-idopyranosiduronyl)-(1→4)-(2-acetamido-2-deoxy-α-D-glucopyranosyl)-(1→4)-(2-O-sulfonato-β-D-glucopyranosiduronyl-(1→4)-(2-acetamido-2-deoxy-α-D-glucopyranosyl)-(1→4)-(2-O-sulfonato-α-L-idopyranosiduronyl)-(1→4)-(2-acetamido-2-deoxy-α-D-glucopyranosyl)-(1→4)-2-O-sulfonato-β-D-glucopyranosiduronate (HS13). $^1$H NMR (600 MHz, D$_2$O): δ 5.39 (d, J=3.6 Hz, 1H), 5.38 (d, J=3.4 Hz, 1H), 5.23-5.20 (m, 2H), 5.14-5.12 (m, 2H), 4.92 (d, J=1.6 Hz, 1H), 4.89 (s, 1H), 4.73 (d, J=7.7 Hz, 1H), 4.63 (d, J=7.9 Hz, 1H), 4.35 (s, 1H), 4.34 (s, 1H), 4.32 (s, 1H), 4.28 (s, 1H), 4.16 (t, J=8.3 Hz, 1H), 4.10 (t, J=8.7 Hz, 1H), 4.06-4.00 (m, 4H), 4.00-3.97 (m, 2H), 3.95-3.90 (m, 5H), 3.88-3.85 (m, 10H), 2.06 (bs, 3H, Ac), 2.04 (bs, 3H, Ac), 2.03 (bs, 3H, Ac), 1.71-1.67 (m, 4H, CH$_2$ linker), 1.52-1.46 (m, 2H, CH$_2$ linker); $^{13}$C NMR (150 MHz, D$_2$O): δ 176.1 (C), 176.02 (C), 175.99 (C), 175.42 (C), 175.37 (C), 175.32 (C), 175.28 (C), 103.3 (CH), 103.09 (CH), 103.06 (CH), 103.03 (CH), 103.0 (CH), 102.9 (CH), 98.1 (CH), 95.5 (CH), 83.1 (CH), 80.9 (CH), 78.4 (CH), 77.9 (CH), 77.8 (CH), 77.7 (CH), 77.6 (CH), 77.5 (CH), 77.3 (CH), 76.2 (CH), 75.2 (CH), 74.62 (CH), 74.57 (CH), 74.1 (CH), 73.0 (CH), 72.2 (CH), 71.2 (CH), 71.1 (CH$_2$), 70.7 (CH), 70.6 (CH), 70.5 (CH), 70.4 (CH), 70.3 (CH), 70.2 (CH), 70.1 (CH), 70.0 (CH), 67.4 (CH$_2$), 67.2 (CH$_2$), 66.9 (CH$_2$), 54.8 (CH), 54.5 (CH), 54.1 (CH), 40.5 (CH$_2$), 29.2 (CH$_2$), 27.3 (CH$_2$), 23.0 (CH$_3$).

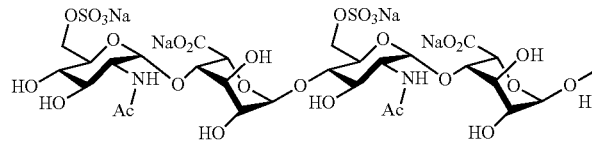
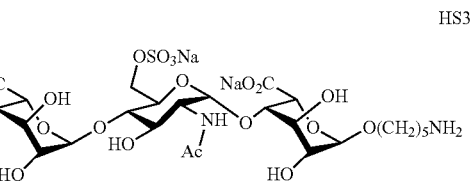

HS3

5-Aminopentyl (2-acetamido-2-deoxy-6-O-sulfonato-α-D-glucopyranosyl)-(1→4)-α-L-idopyranosiduronyl-(1→4)-(2-acetamido-2-deoxy-6-O-sulfonato-α-D-glucopyranosyl)-(1→4)-α-L-idopyranosiduronyl-(1→4)-(2-acetamido-2-deoxy-6-O-sulfonato-α-D-glucopyranosyl)-(1→4)-α-L-idopyranosiduronyl-(1→4)-(2-acetamido-2-deoxy-6-O-sulfonato-α-D-glucopyranosyl)-(1→4)-α-L-idopyranosiduronate (HS3). $^1$H NMR (600 MHz, D$_2$O): δ 5.23-5.10 (m, 7H), 5.03-4.93 (m, 3H), 4.33-4.20 (m, 12H), 4.16-3.96 (m, 11H), 3.95-3.84 (m, 6H), 3.83-3.66 (m, 10H), 3.63-3.58 (m, 2H), 3.10-3.00 (m, 1H), 2.08 (bs, 6H, Ac), 2.04 (bs, 3H, Ac), 2.03 (bs, 3H, Ac), 1.80-1.65 (m, 4H, CH$_2$ linker), 1.52-1.46 (m, 2H, CH$_2$ linker); $^{13}$C NMR (150 MHz, D$_2$O): δ 175.5 (C), 175.3 (C), 175.2 (C), 175.0 (C), 174.8 (C), 174.4 (C), 102.0 (CH), 101.8 (CH), 100.8 (CH), 99.2 (CH), 94.4 (CH), 93.7 (CH), 74.0 (CH), 71.2 (CH), 71.0 (CH), 70.7 (CH), 70.1 (CH), 70.0 (CH), 69.8 (CH), 69.4 (CH), 69.3 (CH), 69.1 (CH), 69.0 (CH), 68.6 (CH), 68.1 (CH), 66.4 (CH), 66.2 (CH), 66.1 (CH$_2$), 53.6 (CH), 53.4 (CH), 53.2 (CH), 53.1 (CH), 39.4 (CH$_2$), 28.0 (CH$_2$), 26.1 (CH$_2$), 22.2 (CH$_3$); HRMS (MALDI): m/z calcd for C$_{61}$H$_{94}$N$_5$O$_{57}$S$_4$ ([M-3H]$^{3-}$): 645.4498, found: 645.4493.

3.79-3.59 (m, 10H), 3.56 (t, J=9.7 Hz, 1H), 3.00 (t, J=7.2 Hz, 2H), 2.08 (s, 3H, Ac), 2.06 (s, 3H, Ac), 2.01 (s, 6H, Ac×2), 1.73-1.59 (m, 4H), 1.52-1.38 (m, 2H); $^{13}$C NMR (150 MHz, D$_2$O): δ 174.8 (C), 174.4 (C), 174.3 (C), 172.7 (C), 101.8 (CH), 100.9 (CH), 99.1 (CH), 99.0 (CH), 98.5 (CH), 95.3 (CH), 94.9 (CH), 76.3 (CH), 76.2 (CH), 73.7 (CH), 73.6 (CH), 71.0 (CH), 70.8 (CH), 70.6 (CH), 70.56 (CH), 69.7 (CH), 69.6 (CH), 68.9 (CH), 68.7 (CH), 68.6 (CH$_2$), 67.4 (CH), 67.3 (CH), 66.5 (CH), 66.3 (CH$_2$), 66.1 (CH$_2$), 53.4 (CH), 53.3 (CH), 53.1 (CH), 39.3 (CH$_2$), 27.9 (CH$_2$), 27.6 (CH$_2$), 26.4 (CH$_2$), 22.2 (CH$_2$), 22.1 (CH$_3$), 21.9 (CH$_3$), 21.8 (CH$_3$); HRMS (ESI): m/z calcd for C$_{61}$H$_{93}$N$_5$O$_{69}$S$_8$ ([M-4H]$^{4-}$): 563.7922, found: 563.7941.

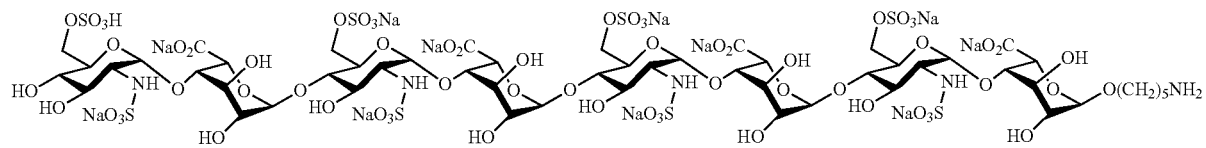

HS4

5-Aminopentyl (2-deoxy-2-sulfamido-6-O-sulfonato-α-D-glucopyranosyl)-(1→4)-α-L-idopyranosiduronyl-(1→4)-(2-deoxy-2-sulfamido-6-O-sulfonato-α-D-glucopyranosyl)-(1→4)-α-L-idopyranosiduronyl-(1→4)-(2-deoxy-2-sulfamido-6-O-sulfonato-α-D-glucopyranosyl)-(1→4)-α-L-idopyranosiduronyl-(1→4)-(2-deoxy-2-sulfamido-6-O-sulfonato-α-D-glucopyranosyl)-(1→4)-α-L-idopyranosiduronate (HS4). $^1$H NMR (600 MHz, D$_2$O): δ 5.38-5.33 (m, 4H), 5.02 (bs, 4H), 4.89 (bs, 2H), 4.51 (d, J=2.4 Hz, 1H), 4.40-4.33 (m, 4H), 4.25-4.17 (m, 4H), 4.16-4.10 (m, 4H), 4.10-4.05 (m, 4H), 4.05-3.93 (m, 5H), 3.88-3.83 (m, 1H), 3.82-3.73 (m, 7H), 3.70-3.65 (m, 5H),

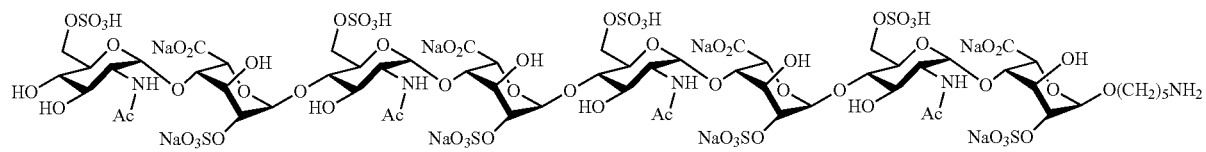

HS5

5-Aminopentyl (2-acetamido-2-deoxy-6-O-sulfonato-α-D-glucopyranosyl)-(1→4)-(2-O-sulfonato-α-L-idopyranosiduronyl)-(1→4)-(2-acetamido-2-deoxy-6-O-sulfonato-α-D-glucopyranosyl)-(1→4)-(2-O-sulfonato-α-L-idopyranosiduronyl)-(1→4)-(2-acetamido-2-deoxy-6-O-sulfonato-α-D-glucopyranosyl)-(1→4)-(2-O-sulfonato-α-L-idopyranosiduronyl)-(1→4)-(2-acetamido-2-deoxy-6-O-sulfonato-α-D-glucopyranosyl)-(1→4)-2-O-sulfonato-α-L-idopyranosiduronate (HS5). $^1$H NMR (600 MHz, D$_2$O): δ 5.24-2.18 (m 5H), 5.18-5.08 (m, 5H), 5.04-4.89 (m, 2H), 4.35-4.20 (m, 13H), 4.15-3.93 (m, 9H), 3.94-3.79 (m, 4H), 3.58 (t, J=9.7 Hz, 1H), 3.30-3.20 (m, 4H), 3.00 (td, J=2.1, 7.5 Hz, 2H), 1.73-1.64 (m, 4H, CH$_2$ linker), 1.49-1.43 (m, 2H, CH$_2$ linker); $^{13}$C NMR (150 MHz, D$_2$O): δ 175.4 (C), 175.2 (C), 101.9 (CH), 100.7 (CH), 95.6 (CH), 95.58 (CH), 95.5 (CH), 77.6 (CH), 77.4 (CH), 77.3 (CH), 71.2 (CH), 69.9 (CH), 69.8 (CH), 69.0 (CH), 68.9 (CH), 68.6 (CH), 68.4 (CH), 68.3 (CH), 68.0 (CH$_2$), 67.8 (CH), 67.5 (CH), 66.4 (CH$_2$), 66.2 (CH$_2$), 57.8 (CH), 57.7 (CH), 39.4 (CH$_2$), 28.0 (CH$_2$), 26.2 (CH$_2$), 22.2 (CH$_3$); HRMS (ESI): m/z calcd for C$_{53}$H$_{78}$N$_5$O$_{65}$S$_8$Na$_8$ ([M+8Na-11H]$^{3-}$): 754.6633, found: 754.6641.

HS14

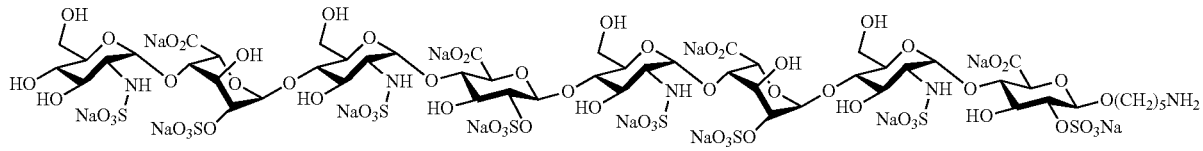

5-Aminopentyl (2-deoxy-2-sulfamido-α-D-glucopyranosyl)-(1→4)-(2-O-sulfonato-α-L-idopyranosiduronyl)-(1-4)-(2-deoxy-2-sulfamido-α-D-glucopyranosyl)-(1→4)-(2-O-sulfonato-β-D-glucopyranosiduronyl-(1→4)-(2-deoxy-2-sulfamido-α-D-glucopyranosyl)-(1→4)-(2-O-sulfonato-α-L-idopyranosiduronyl)-(1→4)-(2-deoxy-2-sulfamido-α-D-glucopyranosyl)-(1→4)-2-O-sulfonato-β-D-glucopyranosiduronate (HS14). $^1$H NMR (600 MHz, D$_2$O): δ 5.61 (d, J=3.7 Hz, 1H), 5.60 (d, J=3.5 Hz, 1H), 5.35-5.32 (m, 2H), 5.27 (bs, 2H), 4.89-4.87 (m, 1H), 4.72 (d, J=7.7 Hz, 1H), 4.64 (d, J=7.8 Hz, 1H), 4.37-4.34 (m, 2H), 4.29-4.25 (m, 2H), 4.18 (t, J=8.5 Hz, 1H), 4.12 (t, J=8.6 Hz, 1H), 4.08-4.04 (m, 3H), 4.01-3.98 (m, 2H), 3.90-3.84 (m, 12H), 3.83-3.80 (m, 4H), 3.77-3.73 (m, 2H), 3.73-3.70 (m, 3H), 3.70-3.65 (m, 5H), 3.48 (t, J=9.5 Hz, 1H), 3.28 (dd, J=10.6, 3.5 Hz, 1H), 3.27-3.22 (m, 3H), 3.02 (t, J=7.4 Hz, 1H), 1.72-1.63 (m, 4H, CH$_2$ linker), 1.57-1.46 (m, 2H, CH$_2$ linker); $^{13}$C NMR (150 MHz, D$_2$O): δ 176.5 (C), 176.2 (C), 175.9 (C), 175.6 (C), 101.8 (CH), 101.7 (CH), 100.2 (CH), 98.9 (CH), 98.3 (CH), 81.1 (CH), 80.7 (CH), 80.6 (CH), 78.4 (CH), 78.2 (CH), 78.1 (CH), 77.9 (CH), 77.5 (CH), 77.4 (CH), 76.6 (CH), 76.2 (CH), 75.9 (CH), 75.7 (CH), 72.7 (CH), 72.3 (CH), 72.2 (CH), 71.7 (CH), 71.10 (CH$_2$), 71.08 (CH), 70.93 (CH), 70.90 (CH), 70.4 (CH), 69.5 (CH), 69.3 (CH), 69.0 (CH), 68.8 (CH), 61.4 (CH$_2$), 60.8 (CH$_2$), 60.4 (CH$_2$), 59.4 (CH), 59.2 (CH), 58.9 (CH), 40.6 (CH$_2$), 29.1 (CH$_2$), 27.5 (CH$_2$), 23.0 (CH$_2$).

HS16

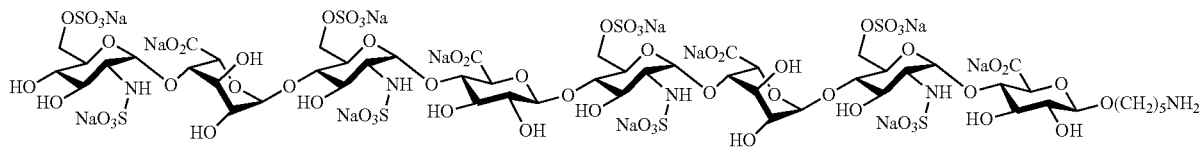

5-Aminopentyl (2-deoxy-2-sulfamido-6-O-sulfonato-α-D-glucopyranosyl)-(1→4)-α-L-idopyranosiduronyl-(1→4)-(2-deoxy-2-sulfamido-6-O-sulfonato-α-D-glucopyranosyl)-(1→4)-β-D-glucopyranosiduronyl-(1→4)-(2-deoxy-2-sulfamido-6-O-sulfonato-α-D-glucopyranosyl)-(1→4)-α-L-idopyranosiduronyl-(1→4)-(2-deoxy-2-sulfamido-6-O-sulfonato-α-D-glucopyranosyl)-(1→4)-β-D-glucopyranosiduronate (HS16). $^1$H NMR (600 MHz, D$_2$O): δ 5.58 (bs, 1H), 5.38-5.32 (m, 2H), 5.04-4.99 (m, 2H), 4.76-4.72 (m, 2H), 4.62-4.58 (m, 2H), 4.46 (d, J=7.9 Hz, 1H), 4.38-4.30 (m, 2H), 4.21-4.17 (m, 3H), 4.12-4.10 (m, 2H), 4.03-4.00 (m, 1H), 3.95-3.92 (m, 1H), 3.88-3.83 (m, 2H), 3.81-3.67 (m, 13H), 3.66-3.62 (m, 2H), 3.58-3.54 (m, 2H), 3.53-3.49 (m, 1H), 3.40-3.36 (m, 1H), 3.34 (d, J=7.7 Hz, 1H), 3.32-3.30 (m, 2H), 3.29-3.24 (m, 3H), 3.21 (dd, J=10.3, 3.3 Hz, 1H), 2.99 (t, J=7.4 Hz, 1H), 1.71-1.60 (m, 4H, CH$_2$ linker), 1.50-1.40 (m, 2H, CH$_2$ linker); $^{13}$C NMR (150 MHz, D$_2$O): δ 176.51 (C), 176.47 (C), 176.1 (C), 176.0 (C), 103.2 (CH), 103.0 (CH), 102.94 (CH), 102.91 (CH), 98.7 (CH), 98.5 (CH), 96.6 (CH), 96.4 (CH), 78.7 (CH), 78.3 (CH), 78.2 (CH), 78.1 (CH), 77.8 (CH), 77.5 (CH), 77.4 (CH), 76.9 (CH), 76.7 (CH), 76.2 (CH), 75.6 (CH), 75.44 (CH), 75.40 (CH), 74.1 (CH), 73.9 (CH), 73.8 (CH), 73.0 (CH), 72.3 (CH), 71.02 (CH$_2$), 70.96 (CH), 70.9 (CH), 70.7 (CH), 70.1 (CH), 70.0 (CH), 69.9 (CH), 69.8 (CH), 69.65 (CH), 69.56 (CH), 69.5 (CH), 68.8 (CH), 67.4 (CH$_2$), 67.3 (CH$_2$), 66.9 (CH$_2$), 59.2 (CH), 58.8 (CH), 58.3 (CH), 40.5 (CH$_2$), 29.2 (CH$_2$), 27.3 (CH$_2$), 23.0 (CH$_2$); HRMS (ESI): m/z calcd for C$_{53}$H$_{79}$N$_5$O$_{65}$S$_8$Na$_6$ ([M+6Na-10H]$^{4-}$): 554.7546, found: 554.7562.

HS11

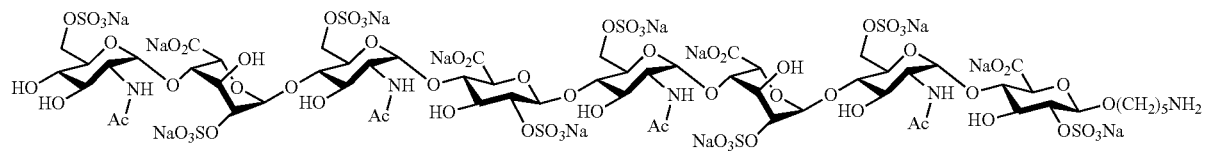

5-Aminopentyl (2-acetamido-2-deoxy-6-O-sulfonato-α-D-glucopyranosyl)-(1→4)-(2-O-sulfonato-α-L-idopyranosiduronyl)-(1→4)-(2-acetamido-2-deoxy-6-O-sulfonato-α-D-glucopyranosyl)-(1→4)-(2-O-sulfonato-β-D-glucopyranosiduronyl)-(1→4)-(2-acetamido-2-deoxy-6-O-sulfonato-α-D-glucopyranosyl)-(1→4)-(2-O-sulfonato-α-L-idopyranosiduronyl)-(1→4)-(2-acetamido-2-deoxy-6-O-sulfonato-α-D-glucopyranosyl)-(1→4)-2-O-sulfonato-β-D-glucopyranosiduronate (HS11). $^1$H NMR (600 MHz, D$_2$O): δ 5.42 (s, 1H), 5.38 (s, 1H), 5.23 (s, 2H), 5.19 (s, 2H), 4.94 (s, 1H), 4.89 (s, 1H), 4.64 (d, J=7.7 Hz, 1H), 4.60 (d, J=10.6 Hz, 1H), 4.40-4.35 (m, 5H), 4.33 (bs, 1H), 4.29-4.25 (m, 5H), 4.18 (t, J=8.4 Hz, 1H), 4.13-4.07 (m, 4H), 4.07-4.00 (m, 6H), 3.98-3.91 (m, 5H), 3.89-3.81 (m, 9H), 3.77 (d, J=9.6 Hz, 1H), 3.75-3.70 (m, 2H), 3.59 (t, J=9.6 Hz, 1H), 3.04 (t, J=7.3 Hz, 2H), 2.09 (bs, 6H, CH$_3$×2), 2.08 (bs, 3H, Ac), 2.07 (bs, 3H, Ac), 1.75-1.66 (m, 4H, CH$_2$ linker), 1.56-1.49 (m, 2H, CH$_2$ linker); $^{13}$C NMR (150 MHz, D$_2$O): δ 176.4 (C), 176.1 (C), 175.8 (C), 175.7 (C), 175.4 (C), 175.3 (C), 101.5 (CH), 101.0 (CH), 100.1 (CH), 100.0 (CH), 98.3 (CH), 98.1 (CH), 95.2 (CH), 94.8 (CH), 81.6 (CH), 81.1 (CH), 78.9 (CH), 77.8 (CH), 77.6 (CH), 77.3 (CH), 77.1 (CH), 76.9 (CH), 76.5 (CH), 76.4 (CH), 75.4 (CH), 74.9 (CH), 73.4 (CH), 72.3 (CH), 72.1 (CH), 71.13 (CH), 71.11 (CH$_2$), 70.5 (CH), 70.4 (CH), 70.34 (CH), 70.30 (CH), 70.26 (CH), 70.1 (CH), 69.2 (CH), 68.9 (CH), 67.5 (CH$_2$), 67.3 (CH$_2$), 66.8 (CH$_2$), 66.3 (CH$_2$), 65.2 (CH$_2$), 54.7 (CH), 54.3 (CH), 54.0 (CH), 40.5 (CH$_2$), 29.0 (CH$_2$), 27.3 (CH$_2$), 23.3 (CH$_3$), 22.97 (CH$_2$), 22.95 (CH$_3$); HRMS (ESI): m/z calcd for C$_{61}$H$_{87}$N$_5$O$_{69}$S$_8$Na$_6$ ([M+6Na-10H]$^{4-}$): 596.7651, found: 596.7657.

HS12

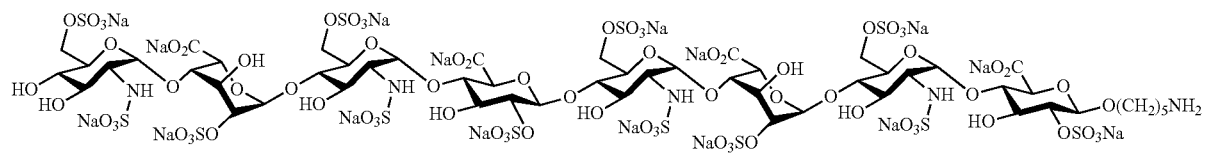

5-Aminopentyl (2-deoxy-2-sulfamido-6-O-sulfonato-α-D-glucopyranosyl)-(1→4)-(2-O-sulfonato-α-L-idopyranosiduronyl)-(1→4)-(2-deoxy-2-sulfamido-6-O-sulfonato-α-D-glucopyranosyl)-(1→4)-(2-O-sulfonato-β-D-glucopyranosiduronyl)-(1→4)-(2-deoxy-2-sulfamido-6-O-sulfonato-α-D-glucopyranosyl)-(1→4)-(2-O-sulfonato-α-L-idopyranosiduronyl)-(1→4)-(2-deoxy-2-sulfamido-6-O-sulfonato-α-D-glucopyranosyl)-(1→4)-2-O-sulfonato-β-D-glucopyranosiduronate (HS12). $^1$H NMR (600 MHz, D$_2$O): δ 5.68 (d, J=3.6 Hz, 1H), 5.64 (d, J=3.6 Hz, 1H), 5.49-5.46 (m, 2H), 5.30 (bs, 2H), 4.98 (d, J=1.08 Hz, 1H), 4.94 (d, J=1.0 Hz, 1H), 4.66 (d, J=7.7 Hz, 1H), 4.60 (d, J=10.8 Hz, 1H), 4.44-4.38 (m, 5H), 4.38-4.34 (m, 2H), 4.33-4.28 (m, 2H), 4.26 (d, J=10.0 Hz, 2H), 4.24-4.20 (m, 3H), 4.16 (dd, J=8.70, 8.19 Hz, 1H), 4.10-4.06 (m, 2H), 4.05-3.98 (m, 6H), 3.98-3.97 (m, 1H), 3.97-3.92 (m, 4H), 3.92 (bs, 1H), 3.91-3.84 (m, 4H), 3.79 (t, J=9.7 Hz, 1H), 3.75-3.70 (m, 1H), 3.61 (t, J=9.7 Hz, 1H), 3.45 (dd, J=10.7, 3.7 Hz, 1H), 3.43-3.38

α-L-idopyranosiduronyl)-(1→4)-(2-deoxy-2-sulfamido-α-D-glucopyranosyl)-(1→4)-2-O-sulfonato-α-L-idopyranosiduronate (HS8). $^1$H NMR (600 MHz, D$_2$O): δ 5.40-5.27 (m, 7H), 5.10 (d, J=2.5 Hz, 1H), 4.93-4.90 (m, 1H), 4.87-4.85 (m, 1H), 4.89-4.87 (m, 1H), 4.48-4.47 (m, 1H), 4.38-4.31 (m, 4H), 4.27-4.20 (m, 4H), 4.19-4.17 (m, 1H), 4.11-4.00 (m, 5H), 3.91-3.80 (m, 12H), 3.78-3.64 (m, 11H), 3.45 (t, J=9.6 Hz, 1H), 3.26-3.20 (m, 4H), 2.99 (t, J=7.9 Hz, 1H), 1.71-1.59 (m, 4H, CH$_2$ linker), 1.50-1.39 (m, 2H, CH$_2$ linker); HRMS (ESI): m/z calcd for C$_{53}$H$_{84}$N$_5$O$_{65}$S$_8$ ([M-5H]$^{5-}$): 417.2238, found: 417.2224.

HS8

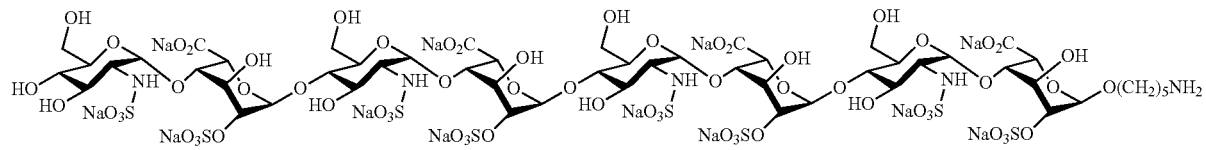

5-Aminopentyl (2-deoxy-2-sulfamido-α-D-glucopyranosyl)-(1→4)-(2-O-sulfonato-α-L-idopyranosiduronyl)-(1→4)-(2-deoxy-2-sulfamido-α-D-glucopyranosyl)-(1→4)-(2-O-sulfonato-α-L-idopyranosiduronyl)-(1→4)-(2-deoxy-2-sulfamido-α-D-glucopyranosyl)-(1→4)-(2-O-sulfonato- (m, 3H), 3.05 (t, J=7.4 Hz, 2H), 1.76-1.66 (m, 4H, CH$_2$ linker), 1.59-1.49 (m, 2H, CH$_2$ linker); $^{13}$C NMR (150 MHz, D$_2$O): δ 176.4 (C), 176.1 (C), 175.6 (C), 101.6 (CH), 101.0 (CH), 99.9 (CH), 99.6 (CH), 97.0 (CH), 96.7 (CH), 92.3 (CH), 92.2 (CH), 81.1 (CH), 80.7 (CH), 78.3 (CH), 78.0

(CH), 77.9 (CH), 77.2 (CH), 77.0 (CH), 76.9 (CH), 76.3 (CH), 76.1 (CH), 76.0 (CH), 74.0 (CH), 73.8 (CH), 71.8 (CH), 71.3 (CH), 71.1 (CH$_2$), 70.8 (CH), 70.7 (CH), 70.4 (CH), 69.8 (CH), 69.5 (CH), 69.3 (CH), 68.7 (CH), 68.3 (CH), 68.2 (CH), 67.14 (CH$_2$), 67.07 (CH$_2$), 66.5 (CH$_2$), 64.0 (CH), 63.6 (CH), 55.4 (CH), 55.2 (CH), 55.0 (CH), 40.5 (CH$_2$), 29.0 (CH$_2$), 27.2 (CH$_2$), 23.0 (CH$_2$).

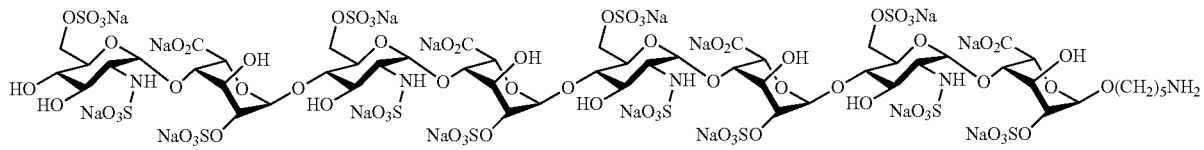

HS6

5-Aminopentyl (2-deoxy-2-sulfamido-6-O-sulfonato-α-D-glucopyranosyl)-(1→4)-(2-O-sulfonato-α-L-idopyranosiduronyl)-(1→4)-(2-deoxy-2-sulfamido-6-O-sulfonato-α-D-glucopyranosyl)-(1→4)-(2-O-sulfonato-α-L-idopyranosiduronyl)-(1→4)-(2-deoxy-2-sulfamido-6-O-sulfonato-α-D-glucopyranosyl)-(1→4)-(2-O-sulfonato-α-L-idopyranosiduronyl)-(1→4)-(2-deoxy-2-sulfamido-6-O-sulfonato-α-D-glucopyranosyl)-(1→4)-2-O-sulfonato-α-L-idopyranosiduronate (HS6). $^1$H NMR (600 MHz, D$_2$O): δ 5.43-5.36 (m 4H), 5.24-5.15 (m, 4H), 5.09-5.04 (m, 2H), 4.76-4.75 (m, 2H), 4.48-4.46 (m, 1H), 4.43-4.29 (m, 7H), 4.28-4.15 (m, 9H), 4.12-3.95 (m, 8H), 3.83-3.71 (m, 5H), 3.69-3.60 (m, 5H), 3.54 (t, J=9.4 Hz, 1H), 3.29-3.19 (m, 4H), 3.01-2.93 (m, 2H), 1.69-1.51 (m, 4H), 1.47-1.39 (m, 2H); $^{13}$C NMR (150 MHz, D$_2$O): δ 99.0 (CH), 97.7 (CH), 97.3 (CH), 97.2 (CH), 96.8 (CH), 76.4 (CH), 76.3 (CH), 76.2 (CH), 76.1 (CH), 76.0 (CH), 75.9 (CH), 75.8 (CH), 75.4 (CH), 68.9 (CH), 68.8 (CH), 68.6 (CH), 68.2 (CH$_2$), 66.4 (CH$_2$), 66.3 (CH$_2$), 57.9 (CH), 39.4 (CH$_2$), 27.8 (CH$_2$), 26.2 (CH$_2$), 22.2 (CH$_2$); HRMS (ESI): m/z calcd for C$_{53}$H$_{73}$N$_5$O$_{77}$Si$_2$Na$_4$H$_{12}$ ([M+4Na-9H]$^{5-}$): 498.7747, found: 498.7736.

Example 2 the Sulfated Octasaccharides of Example 1 May Induce Axon Outgrowth

In this example, the effect of HS1, HS6, HS10 and HS14 of example 1 in rescuing the dystrophic endballs were investigated. It was found that octasaccharides HS6, HS10 and HS14 were capable of inducing phosphorylation of RPTPσ (FIG. 1, panel a), HS16 and HS 14 were further found to prevent formation of dystrophic endballs in adult DRG neurons and facilitated their penetration across the gradient (FIG. 1, panel b). Nearly half of the axons invading the aggrecan rim could pass the rim of aggrecan gradient (FIG. 1, panel c, left), which was comparable to the results when chondroitin sulfate (CS) was digested with chondroitinase ABC (C-ABC) (FIG. 1, panel c, right).

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A sulfated octasaccharide of formula (I), a pharmaceutically acceptable salt, solvate or ester thereof:

(I)

wherein R$^1$ is —NHAc or —NHSO$_3$H; and R$^2$ and R$^3$ are independently H, or —SO$_3$Na.

2. The sulfated octasaccharide of claim 1, wherein R$^1$ is —NHAc; and R$^2$ and R$^3$ are independently —SO$_3$Na.

3. The sulfated octasaccharide of claim 1, wherein R$^1$ is —NHSO$_3$H, R$^2$ is H, and R$^3$ is —SO$_3$Na.

4. The sulfated octasaccharide of claim 1, wherein R$^1$ is —NHSO$_3$H; and R$^2$ and R$^3$ are independently —SO$_3$Na.

5. The sulfated octasaccharide of claim 1, wherein R$^1$ is —NHSO$_3$H, R$^2$ and R$^3$ are independently H.

6. A method of inducing the outgrowth of a neuron comprising contacting the neuron with an effective amount of the sulfated octasaccharide of claim 1, wherein, the sulfated octasaccharide binds to receptor-type protein tyrosine phosphatase σ (RPTPσ).

7. The method of claim 6, wherein in the sulfated octasaccharide of formula (I), R$^1$ is —NHAc, and R$^2$ and R$^3$ are independently —SO$_3$Na.

8. The method of claim 6, wherein in the sulfated octasaccharide of formula (I), R$^1$ is —NHSO$_3$H, R$^2$ is H, and R$^3$ is —SO$_3$Na.

9. A method of treating a neurodegenerative disease in a subject comprising administering to the subject an effective amount of the sulfated octasaccharide of claim 1 to induce the outgrowth of an injured neuron, wherein the neurodegenerative disease is Amyotrophic lateral sclerosis, Alzheimer disease, bovine spongiform encephalopathy, Creutzfeldt-Jakob disease, frontotemporal lobar degeneration, Huntington disease, Lewy body dementia, multiple sclerosis, Parkinson disease, or Pick's disease.

10. The method of claim 9, wherein in the sulfated octasaccharide of formula (I), $R^1$ is —NHAc, and $R^2$ and $R^3$ are independently —SO$_3$Na.

11. The method of claim 9, wherein in the sulfated octasaccharide of formula (I), $R^1$ is —NHSO$_3$H, $R^2$ is H, and $R^3$ is —SO$_3$Na.

* * * * *